United States Patent [19]

Durenec

[11] 4,206,609

[45] Jun. 10, 1980

[54] CRYOGENIC SURGICAL APPARATUS AND METHOD

[75] Inventor: Peter Durenec, Annandale, Va.

[73] Assignee: Actus, Inc., Florence, Ky.

[21] Appl. No.: 938,782

[22] Filed: Sep. 1, 1978

[51] Int. Cl.² .......................... F25B 9/00; F25D 3/00; F25B 19/00

[52] U.S. Cl. .......................................... 62/6; 62/293; 62/514 R; 128/303.1

[58] Field of Search ............................ 62/6, 293, 514; 128/303.1; 60/517

[56] References Cited

U.S. PATENT DOCUMENTS

| | | | |
|---|---|---|---|
| Re. 28,657 | 12/1975 | Barger et al. | 128/303.1 |
| 3,423,948 | 1/1969 | Cowans | 62/6 |
| 3,630,041 | 12/1971 | Daniels | 62/6 |
| 3,650,118 | 3/1972 | O'Neil | 62/6 |
| 3,662,755 | 5/1972 | Rautenbach et al. | 128/303.1 |
| 3,823,575 | 7/1974 | Parel | 62/514 |
| 3,849,652 | 11/1974 | Dix et al. | 250/352 |
| 3,862,546 | 1/1975 | Daniels | 62/6 |
| 3,877,239 | 4/1975 | Leo | 62/6 |
| 3,889,680 | 6/1975 | Armao | 128/303.1 |
| 3,991,586 | 11/1976 | Acord | 62/6 |
| 3,993,075 | 11/1976 | Lisenbee et al. | 128/303.1 |
| 4,029,102 | 6/1977 | Barger | 128/303.1 |
| 4,092,829 | 6/1978 | Durenec . | |
| 4,092,833 | 6/1978 | Durenec | 62/6 |

OTHER PUBLICATIONS

*Application of Closed-Cycle Cryocoolers to Small Superconducting Devices*, NBS Special Publication 508–from conference held Oct. 3–4, 1977.

*Primary Examiner*—Lloyd L. King
*Attorney, Agent, or Firm*—Fleit & Jacobson

[57] ABSTRACT

A cryogenic surgical apparatus using a Sterling-cycle refrigerator connected by elongate flexible conduits to a cryosurgical device having an operating probe. The refrigerator includes a compressor having first and second cylinders with pistons positioned therein. The cryosurgical device includes a housing defining an expansion cylinder. An expansion piston and seals are positioned within the cylinder in such manner that first and second distinct expansion spaces are defined between opposite ends of the piston and ends of the cylinder. The operating probe is connected to or positioned on the end of the housing closest to the first expansion space. A regenerator is positioned in the end of the expansion piston closest to the first expansion space and has an outlet communicating with the first expansion space and an inlet communicating with a space intermediate the two expansion spaces. First and second flexible conduits connect the first and second cylinders of the refrigerator, respectively, to portions of the housing in communication with the inlet to the regenerator and the second expansion space. The first cylinder has a larger cross-sectional area than the second cylinder so that the operating probe is cooled when the compressor rotates in a first direction and is heated when the compressor rotates in an opposite direction. The phase relationship between the two pistons of the refrigerator is selected in such manner that movement of the expansion piston in a direction from the first towards the second of the two expansion spaces is opposed by an increasingly large pressure in the second expansion space.

14 Claims, 4 Drawing Figures

CRYOGENIC SURGICAL APPARATUS AND METHOD

BACKGROUND OF THE INVENTION

1. Field of the Invention

This invention relates to a cryogenic surgical apparatus utilizing a split-cycle mechanical cooler to obtain desired cryogenic operating temperatures. More particularly, this invention relates too such an apparatus that utilizes a refrigerator or cooler utilizing a closed split-cycle Sterling-cycle to obtain desired cryogenic temperatures within a cryosurgical device connected by flexible conduits to the refrigerator.

2. Description of the Prior Art

Sterling-cycle refrigerators or coolers have been previously used in a variety of cryogenic applications, including air liquification systems, pre-cooling for helium liquifiers, mazer cooling and infra-red detector cooling systems.

As is well-known, such coolers utilizes the periodic compression and expansion of a refrigerant within a closed system to generate required temperatures. A piston or displacer is mounted for free movement within a housing, with one end of the piston defining a cold volume between the interior of the housing and one end of the piston. The end of the housing containing the cold volume is provided with a special coating or a "cold finger" to utilize cryogenic temperature generated by the expansion of a refrigerant within the cold volume. A compressor is connected to the housing to reciprocate the piston between compression and expansion strokes. U.S. Pat. No. 4,092,829, entitled "Balanced Compressor" and U.S. Pat. No. 4,092,833, entitled "Split-phase Cooler With Expansion Piston Motion Enhancer" describe coolers of the aforementioned type.

One problem encountered with such coolers is that the movement of the piston away from the "cold finger" during expansion must be stopped and reversed at the start of the compression portion of the Sterling-cycle U.S. Pat. No. 3,991,586, entitled "Solenoid Controlled Cold Head for a Cyrogenic Cooler", describes two different methods for controlling reciprocal movement of the piston or displacer. One method, which is sometimes called a "split cycle" method, utilizes an enclosed pneumatic volume defined in the housing at the end opposite the end having the cold volume. As the cold volume expands during an expansion stroke, gas or refrigerant within the enclosed portion is compressed. Finally, the pressure within the enclosed portion reaches a level sufficiently high to stop movement of the piston or displacer. Some other patents disclosing coolers utilizing a split cycle or pneumatic volume to control movement of the piston or displacer are U.S. Pat. Nos. 3,630,041, 3,862,546, and 3,877,239. A problem encountered with this method is the difficulty of accelerating the piston in the opposite direction after its motion has been stopped. Another problem is heat build up in the pneumatic volume. This problem has been "solved" in some devices by adding heat radiating fins to the exterior of the pneumatic volume. This "solution", of course, increases the size of the device.

The second method described in U.S. Pat. No. 3,991,586 for controlling movement of the piston or displacer uses a spring and a solenoid. The spring and solenoid are associated with the end of the piston spaced farthest from the cold volume. The spring urges the piston in one direction while the solenoid, when energized, overcomes the spring force and urges the piston in the opposite direction.

Numerous problems are encountered with both of these methods for controlling movement of the piston. For instance, large acceleration and deceleration forces are encountered due to the frequency of vibration of the piston. Also, vibration microphonics are generated. Further, there is a tendency for heat to build up due to the friction forces generated during movement of the piston.

Another problem is encountered in the selection of appropriate seal friction. Seal friction delays displacer motion relative to the pressure wave and creates a phase shift between displacement and pressure. The correct amount of seal friction is critical with previously known systems because too little friction results in premature displacer motion, while excessive friction results in no motion. Further, the seal friction is difficult to maintain at desired levels because of wear caused by movement of the displacer.

Turning now to still another problem encountered with Sterling-cycle coolers, large size and complexity make these coolers unsuitable for use in cryosurgery, which requires relatively small, easily manipulated devices.

Also known are cryogenic apparatus, often called cyrosurgical devices, for use in surgical and similar cases that utilize the Joule-Thomson cooling effect provided by the passing of gas under high pressure through an orifice, or plug. The gas, after passing through the orifice, expands into a relatively unrestricted area. Since the expanded gas is vented into the atmosphere, the system is called an open cycle system. U.S. Patents showing such cyrosurgical devices include U.S. Pat. Nos. 3,662,755, 3,823,575, 3,889,680, 3,993,075, and Re. 28,657.

Problems encountered with cyrosurgical devices utilizing an open cycle include the need to provide compressed gases for the devices, the need to exhaust expanded gases without contaminating an operating room environment, and the need to exhaust the gases in such a manner that surfaces contacted by the exhausted gases are not cooled to a dangerously low temperature. Also, it has been found that a technician is required to constantly monitor the rate at which gases are released through the devices in order to ensure that operating tools are maintained at desired temperatures. Further, when different gases are used, different flow rates are required.

SUMMARY OF THE INVENTION

Accordingly, it is an object of the present invention to overcome the disadvantages of the previously known cryogenic surgical apparatus and devices.

More particularly, it is an object of the present invention to provide an improved cryosurgical apparatus utilizing a closed split-cycle mechanical cooler or a closed Sterling-cycle refrigerator to obtain required cryogenic temperatures.

It is another object of the invention to provide an improved cryosurgical device for use with a Sterling-cycle refrigerator.

In accordance with the present invention, a Sterling-cycle refrigerator is connected by elongate flexible conduits to a cryosurgical device having a housing supporting a cryosurgical probe. The refrigerator has a compressor with first and second cylinders having pistons positioned in the cylinders. The compressor is rotatable in a first direction to cool the probe, and is rotatable in the opposite direction to heat the probe. The housing supporting the probe defines an expansion cylinder having a displacer or expansion piston movable therein. First and second distinct expansion chambers or spaces are formed between opposite ends of the piston and ends of the cylinder. The cryosurgical probe is positioned on, supported by, or connected to the end of the housing closest to the first expansion space. Also, a regenerator is positioned in the end of the expansion piston facing the first expansion space. The inlet of the regenerator communicates with a space intermediate the ends of the housing, the space being separated by seals from the two expansion chambers. The outlet of the regenerator communicates with the first expansion chamber. First and second flexible conduits connected the first and second cylinders of the refrigerator, respectively, to the intermediate and second expansion spaces in the cylinder. The first cylinder of the compressor has a larger cross-sectional area than the second cylinder. The phase relationship between the two pistons is selected in such manner that movement of the expansion piston in a direction from the first towards the second of the two expansion spaces is first assisted by decreasing pressure and then opposed by increasing pressure in the second expansion space. The increasing pressure in the second expansion space, after stopping movement of the expansion piston, exerts a force on the expansion piston tending to accelerate the piston towards the first expansion space.

In one embodiment of applicant's invention, a heat exchange relationship is maintained between the first and second conduits and/or between the first conduit and the second expansion space so that, during cooling, refrigerant in the first conduit is pre-cooled prior to entering the intermediate space.

In another embodiment of applicant's invention, the probe is formed of a plurality of expansion spaces interconnected in such manner that each space provides a progressively lower temperature. Preferably, each space has a smaller cross-sectional area to facilitate use of the probe to perform delicate surgery.

In still another embodiment of applicant's invention, pre-cooling of the refrigerant is combined with a probe formed of a plurality of spaces or stages. With this embodiment, gas or coolant is compressed and heated to a temperature of approximately 300° K. by the first cylinder of the compressor. The first conduit containing the compressed gas is wrapped around the second expansion space to pre-cool the compressed gas or coolant to a temperature of approximately 220° K. The compressed gas then expands and cools in the first stage to a temperature of approximately 30° K. Continued expansion in the second stage provides a temperature of approximately 7° K.

After the probe has been used to perform a surgical operation, a brushless D.C. motor controlling the compressor of the refrigerator can be reversed to heat up the probe to facilitate its removal from the object being treated. Also, the speed of rotation of the motor can be varied to control temperatures created within the probe.

Use of the apparatus of the present invention results in lower microphonics and lower thermophonics. When pre-cooling is used, thermophonics can be reduced even more. Also, it is possible to use lower pre-charge pressures within the apparatus. Thus, the apparatus operates at a high efficiency level.

The invention, and its objects and advantages, will become more apparent in the detailed description of the preferred embodiments presented below.

BRIEF DESCRIPTION OF THE DRAWINGS

In the detailed description of the preferred embodiments of the invention presented below, reference is made to the accompanying drawings, in which.

DESCRIPTION OF THE PREFERRED EMBODIMENTS

Figure 1:
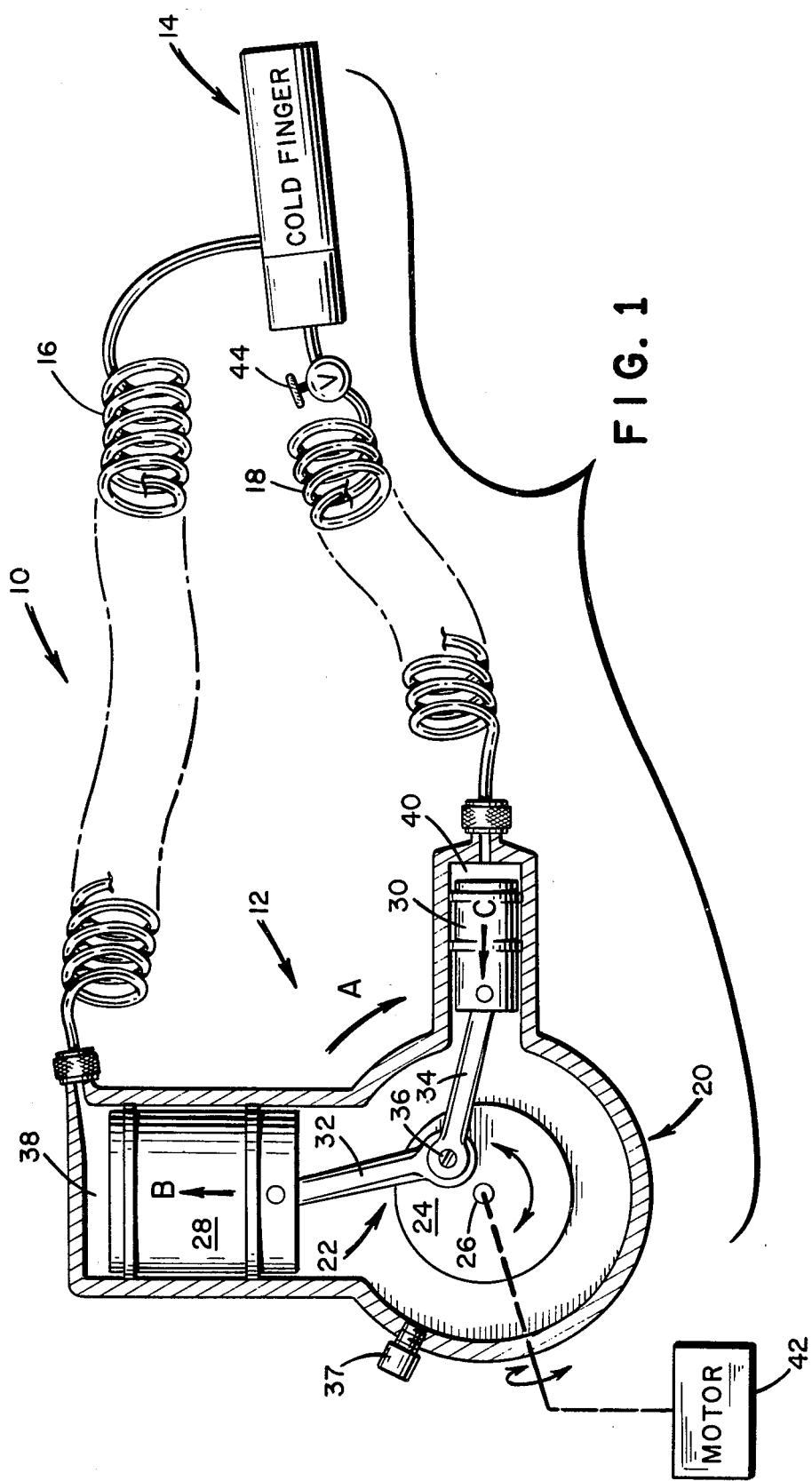
FIG. 1 is a schematic illustration, partially in cross section, of one embodiment of a cryogenic apparatus according to the present invention.

Because cryogenic apparatus are well known, the present description will be directed in particular to elements forming part of, or cooperating more directly with, the present invention. Elements not specifically shown or described herein are understood to be selectable from those known in the art.

Referring now to the drawings, and to FIG. 1 in particular, one embodiment of the present invention is illustrated and will be described in connection with a cryogenic apparatus, generally designated 10.

The cryogenic apparatus 10 has a split-cycle mechanical compressor or refrigerator section, generally designated 12; a cryosurgical operating device or "cold finger", generally designated 14; and a pair of flexible conduits or high pressure tubes 16, 18 interconnecting the refrigerator section 12 and the operating device 14. The refrigerator 12 compresses refrigerant or coolant that subsequently expands in the device 14 to obtain cryogenic operating temperatures.

Considering the refrigerator section 12 in more detail, it includes a housing, generally designated 20, in which a compressor, generally designated 22, has a plate 24 mounted for rotation about a shaft 26. Pistons 28 and 30 of the compressor 22 are connected by arms 32 and 34, respectively, to a shaft 36 for eccentric rotation about the shaft 26. The housing 20 is provided with a fitting 37 that is connectable to a source of pressurized refrigerant or coolants, such as argon, oxygen, helium, hydrogen, methane, neon, nitrogen or air. Preferably, the apparatus is precharged to a pressure of approximately 150 psi. If desired, a lower pre-charge pressure can be used, depending on the design parameters of the system.

As can be seen from FIG. 1, the pistons 28, 30 are reciprocable within cylinders 38, 40, respectively, defined within the housing 20. Preferably, the cylinders are separated by a 90° angle. A motor 42, which is preferably a brushless DC motor operating in a helium atmosphere, rotates plate 24 at a speed between approximately 1200 and 1500 rpm. As plate 24 rotates, pistons 28, 30 are reciprocated within the cylinders 38, 40. As will be discussed in more detail hereinafter, when the motor rotates plate 24 in the direction of arrow A in FIG. 1, the operating device 14 is cooled. Also, the motor 42 can be reversed to rotate plate 24 in a direction opposite that of arrow A to heat the operating device, thereby facilitating its removal from a patient undergoing surgery.

As also illustrated in FIG. 1, the conduits 16, 18 connect the cylinders 38, 40, respectively, to portions of the operating device 14. Preferably, a valve 44 is associated with the conduit 18 to facilitate adjustment of the system to compensate for the wear of components within the operating device 14. In one embodiment of applicant's invention, the conduits are made of stainless steel and have a length of between 16 and 20 inches, an inside diameter of approximately 0.29 inches, and a wall thickness of approximately 0.08 inches. The conduits allow separation of the operating device 14 from the refrigerator section 12, so that the size of the operating device 14 can be reduced to a size suitable for use in a delicate surgical operation.

Figure 2:
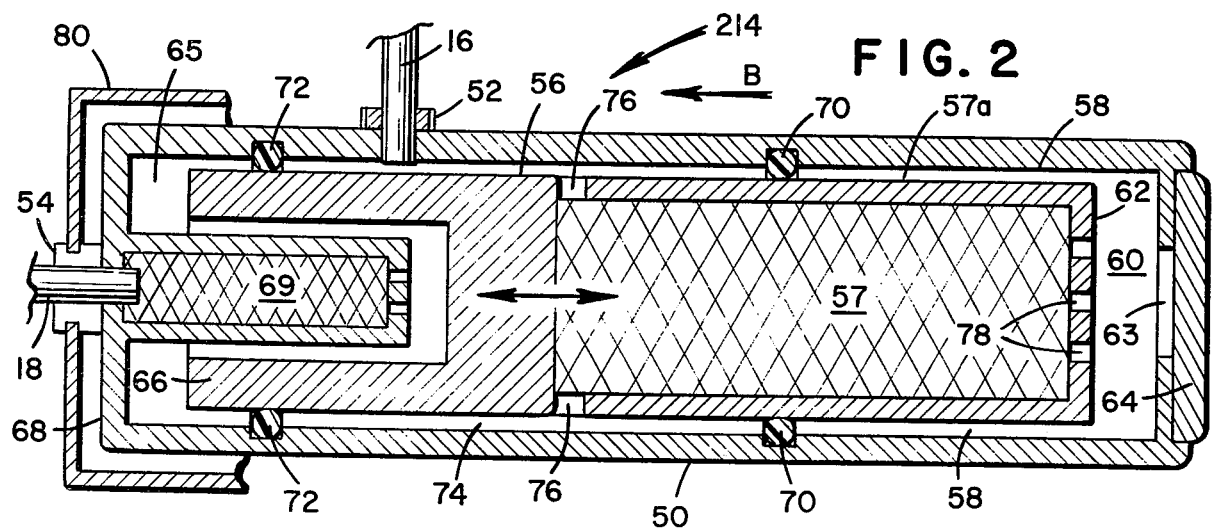
FIG. 2 is an enlarged, cross-sectional view of one embodiment of a cryosurgical device used with the apparatus of FIG. 1.

Turning now to a consideration of FIG. 2, this Figure illustrates an embodiment of the operating device 14, which is generally designated 214. The operating device 214 has an elongated, preferably cylindrical, housing 50 with a first opening or fitting 52 adapted to connect the housing to conduit 16, and a second fitting or opening 52 adapted to connect the housing to conduit 18. A free-floating displacer or expansion piston 56 is positioned for reciprocal movement in a cylinder or bore 58 defined within the housing 50. The piston 56 includes a regenerator 57 of a known type, such as a fiberglass housing 57a surrounding a stainless steel screen or a fiberglass housing filled with lead or nickel balls, preferably sintered to increase their surface area. A first space or "cooled volume" 60 is defined between the leading end 62 (right end as viewed in FIG. 2) of the piston 56 and one end 63 of the housing. A portion 64 of end 63 is formed of a conducting material, such as copper, to transfer temperatures from the space 60 to an exterior surface of the housing. The exterior of portion 64 acts as a surgical probe or instrument. A second space 65 is defined between the trailing end 66 of the piston and the other end 68 of the housing. Preferably, a second regenerator 69 is positioned in the second space and communicates the second space with conduit 18. Sealing rings 70 and 72 define an intermediate space between and separate from the spaces 60 and 65. The regenerator 57 includes first openings or passageways 76 communicating with intermediate space 74 and second openings or passageways 78 communicating with the first space 60. To slow down undesired radiation from the housing 50, the walls of the housing are super insulated and/or the housing is surrounded by a vacuum jacket, a portion of which, designated 80, is illustrated.

Figure 3:
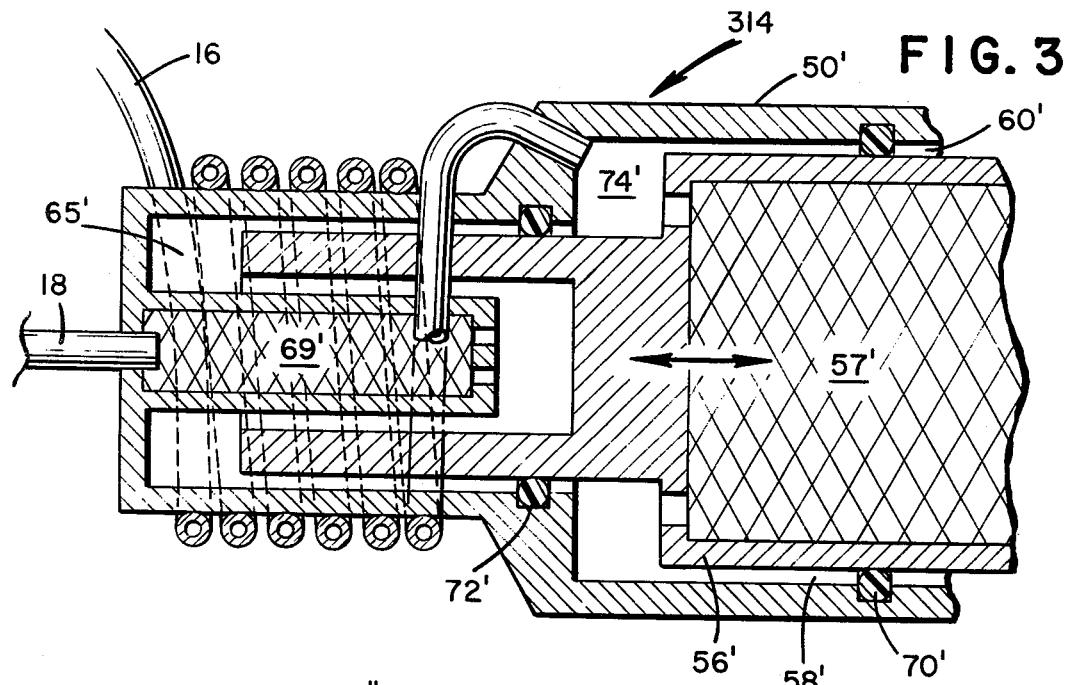
FIG. 3 is an enlarged cross-sectional view of a portion of another embodiment of a cryosurgical device used with the apparatus of FIG. 1.

Considering now the embodiment illustrated in FIG. 3, which is generally designated 314, the same reference numbers, with primes, have been used to identify components previously discussed in connection with the description of FIG. 2. As illustrated in FIG. 3, a free-floating displacer or expansion piston 56' in positioned for reciprocal movement in a cylindrical passage or bore 58' defined within a housing 50'. Seals 70' and 72' define a first space or "cooled volume" 60', a second space 65', and an intermediate space 74'. The conduit 18 communicates with the second space 65' through a regenerator 69', while the conduit 16 communicates with the intermediate space 74'. The right or front end of the operating device 314 is basically the same as the right or front end of the operating device 214 and has not been illustrated.

The basic difference between the embodiment illustrated in FIG. 2 and that illustrated in FIG. 3 is that the conduit 16 has been wrapped in a helical manner around a portion of housing 50' defining the second space 65', prior to its connection to the portion of housing 50' containing intermediate space 74'. During a cooling operation, the second space 65' is cooled by refrigerant compressed by piston 30 (FIG. 1) prior to the first space 60' being cooled by refrigerant compressed by piston 38. Thus, by wrapping conduit 16 around the housing, refrigerant in conduit 16 is pre-cooled prior to the refrigerant entering intermediate space 74'. For example, if the coolant in conduit 16, as it leaves the refrigerator section 12, has a temperature of approximately 300° K., the pre-cooling reduces the temperature to approximately 220° K. Also, by using pre-cooling, it is possible to use lower pre-charge pressures within the apparatus. Further, it has been found that the pre-cooling increases efficiency by approximately 25%.

Figure 4:
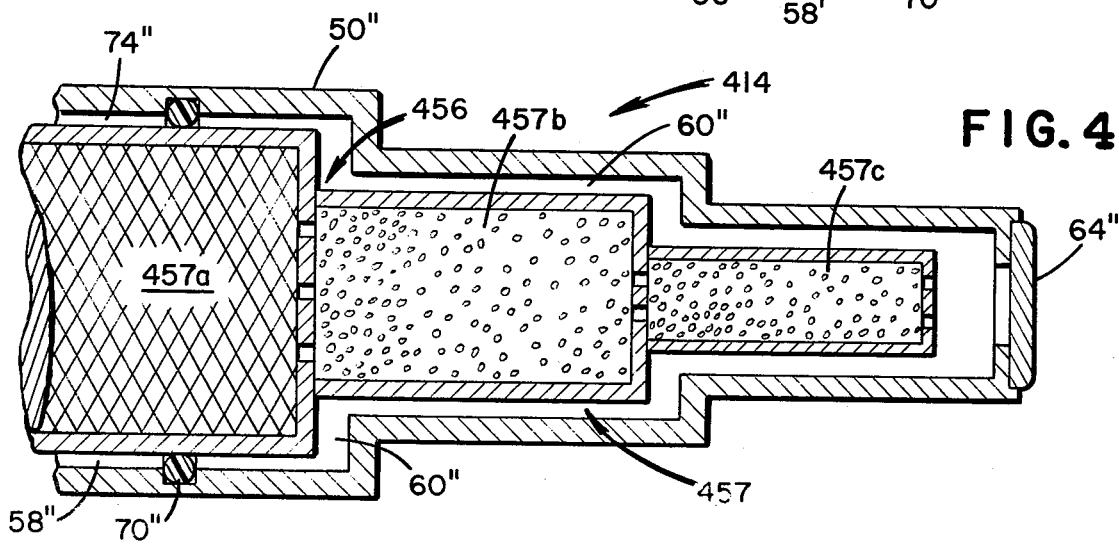
FIG. 4 is an enlarged, cross-sectional view of a portion of still another embodiment of a cryosurgical device utilized with the apparatus of FIG. 1.

Referring now to FIG. 4, another embodiment of the operating device, which is generally designated 414, is illustrated. This embodiment is similar to the embodiments illustrated in FIGS. 2 and 3, and the same reference numbers, with double primes, have been used to identify similar components. Since the embodiment illustrated in FIG. 4 is basically a modification of the right-hand portion of the embodiments illustrated in FIGS. 2 and 3, only the right-hand portion of the operating device 414 has been illustrated.

As illustrated, the operating device 414 has a housing 50", defining a bore 58" in which a free-floating displacer or expansion piston 456 is positioned for reciprocal movement. A first seal 70" and a second seal (not shown) are positioned in such manner as to define a first space 60", an intermediate space 74" and a second space (not shown) within the housing 50". The right-hand portion of the piston 456 includes a multi-stage regenerator, generally designated 457. The multi-stage regenerator 457 has a first section 457a with a regenerator formed of a stainless steel screen positioned within a fiberglass housing, a second section 457b formed of nickel balls positioned within a fiberglass housing, and a third section 457c formed of lead balls positioned within a fiberglass housing. By using a multi-stage regenerator, lower temperatures can be obtained than with a single-stage regenerator of the type illustrated in FIG. 2. For instance, temperatures as low as 7° K. can be obtained with the embodiment illustrated in FIG. 4.

Since the embodiments illustrated in FIGS. 3 and 4 operate in a manner similar to the embodiment illustrated in FIG. 2, only the operation of the FIG. 2 embodiment will be described. The attention of the reader is therefore directed to FIGS. 1 and 2.

When it is desired to use the cryogenic apparatus 10 to freeze a member during a surgical operation, the apparatus is pre-charged, for instance, with helium gas, to a pressure of approximately 150 psi by connecting a pressurized source of helium to the fitting 37. The motor 42 is then energized to reduce temperatures within the apparatus to desired levels. As motor 42 rotates plate 24, pistons 28, 30 attached to the plate alternately compress and expand the gas within the apparatus 10. Gas compressed by piston 28 to approximately 300 psi passes through conduit 16 into intermediate space 74 and then enters regenerator 57 through openings 76. After passing through regenerator 57, the compressed gas expands within the first space 60. As the gas expands, temperatures within the space 60 drop, and the temperature of the temperature-conducting portion 64 of end 63 correspondingly drops. By varying the speed of revolution of the motor 42, precise control can be had over the temperature of portion 64. It should be noted that normally, an initial cooling period of as long as three to five minutes is required before the device can be used.

In a similar manner, gas compressed by piston 30 is fed through conduit 18 into the second space 65. During the initial portion of the movement of piston 56 from its rightmost position in FIG. 2 towards its leftmost position, the pressure within chamber 65 is decreasing thereby facilitating the initial movement. Because of the phase difference between the pistons 28 and 30, continued movement of the piston 56 to the left will be opposed by increasing pressure within the second space 65; however, since the piston 28 has a larger surface area than the piston 30, the initial buildup of pressure in space 65 will not prevent continued movement of piston 56. As piston 56 continues to move to the left, pressure within first space 60 changes until a point is reached at which the pressure buildup within the space 65 is sufficiently large that movement of piston 56 towards the left is stopped, and the piston is moved back towards the right. The point at which this reversing motion starts can be adjusted by changing the setting of valve 44. Thus, valve 44 provides a mechanism for adjusting the apparatus 10 to compensate for wear of the seals 70 and 72. Further, use of the pressure within space 65 provides a method both for stopping the movement of piston 56 in one direction and for assisting movement in the opposite direction. Also, the pressure within space 65 prevents contact between piston 56 and end 68 of the housing, thereby virtually eliminating microphonics.

Numerous advantages are provided by the improved apparatus of the present invention. For instance, the system requires operating pressures of approximately 300 psi. Thus, a smaller compressor can be used than in previously known systems which required pressures of approximately 600 psi. Use of lower pressures reduces the problems caused by seal leakage and reduces the problems of microphonics and thermophonics. Further, by pre-cooling the refrigerant before it enters the regenerator, lower temperatures can be obtained without a significant increase in expended energy. Since the temperature of the operating device is directly controlled by the rpm of the motor used in the refrigerator section of the apparatus, control of operating temperatures is greatly simplified. Further, since the operating device can be heated by reversing the polarity of the motor, removal of the operating device at the completion of a surgical operation is greatly facilitated. By using a multi-stage regenerator of the type illustrated in FIG. 4, lower operating temperatures can be obtained because the risk of the refrigerant freezing is greatly reduced by the staged expansion of the refrigerant within the multistage regenerator.

The invention has been described in detail with particular reference to preferred embodiments thereof, but it will be understood that variations and modifications can be effected within the spirit and scope of the invention.

What is claimed is:

1. An apparatus for use in a cryogenic surgical operation, the apparatus comprising a closed fluidically controlled Stirling cycle cooling system having a compression portion, a distinct expansion portion spaced from the compression portion, and flexible conduit means for interconnecting the compression and expansion portions, said compression portion comprising:
    a first piston positioned in a first cylinder,
    a second piston smaller than said first piston positioned in a second cylinder, and
    means for reciprocally moving said pistons to compress refrigerant in said cylinders, said pistons being moved in such manner that there is a 90° mechanical phase difference in the movement of said pistons;
said expansion portion comprising:
    a third cylinder having distinct first, intermediate, and second spaces,
    a third piston positioned in said third cylinder having opposite ends positioned in said first and second spaces, respectively, said third piston being displaceable in said third cylinder by the movement of said first and second pistons,
    a regenerator positioned in said end of said third cylinder which is in said first space and in communication with said intermediate and said first spaces,
    seal means for separating said first and said intermediate spaces and for separating said second and said intermediate spaces, and
    an exterior portion of said third cylinder being in heat exchange relationship with said first space and defining a probe for use in a cryogenic surgical operation, the probe being selectively heated and cooled by controlling the direction of movement of said first and said second pistons; and
said flexible conduit means comprising:
    first conduit means for interconnecting said first cylinder and said intermediate space, and
    second conduit means for interconnecting said second cylinder and said second space so that displacement of said third piston in a direction from said first towards said second space is initially assisted by the pressure in said second space and subsequently opposed by the pressure in said second space.

2. An apparatus for use in a cryosurgical operation, the apparatus comprising:
    compressing means using a Stirling cycle for compressing a refrigerant used to obtain cryosurgical operating temperatures;
    an operating device having a portion thereof adapted for use as a surgical implement in a cryosurgical operation; and
    first and second flexible conduit means for interconnecting said compressing means and said operating device so that said operating device can be moved independently of said compressing means;
    said compressing means comprising:
        a housing having a first portion thereof defining a first cylindrical bore and first port means for connecting said first cylindrical bore and said first conduit means, and a second portion thereof defining a second cylindrical bore and second port means for connencting said second cylindrical bore and said second conduit means, the cross-sectional area of said second cylindrical bore being less than the cross-sectional area of said first cylindrical bore;
    means connected to said housing for adding refrigerant to said housing; and
    compressor means having first and second pistons positioned in said first and said second cylindrical bores, respectively, and having compression strokes for compressing refrigerant, and means for reciprocating said pistons so that a predetermined phase relationship is maintained between the compression strokes of said pistons, said means for reciprocating being controllable to selectively cool and heat the surgical device;

said operating device comprising:
a housing having an interior wall forming a bore with first, intermediate, and second spaces defined therein, first conduit port means for connecting the intermediate space of said bore and said first conduit means, second conduit port means for connecting the second space of said bore and said second conduit means, and a portion of the housing surrounding the first space being in heat exchange relationship with the surgical implement;
a displacer positioned in said bore for reciprocal movement, said displacer including a regenerator in communication with said intermediate and said first spaces;
first and second seal means for supporting said displacer in a position radially spaced from the interior wall of said housing; said first seal means cooperating with said displacer to separate said first and said intermediate spaces so that refrigerant compressed by said first piston passes from said first cylindrical bore through said first conduit, said intermediate space, and said regenerator and expands into said first space thereby creating cryogenic operating temperatures; and said second seal means cooperating with said displacer to separate said intermediate and said second spaces so that increasing pressure in said second space, as a result of the phase relationship between the compression strokes of said pistons, prevents contact between an end of said displacer and an end of said housing.

3. An apparatus according to claim 2 wherein said second conduit means includes valve means for controlling the rate of increase of pressure in said second space.

4. An apparatus according to claim 2 wherein said means for reciprocating said pistons includes a rotatable plate and wherein said pistons have rods eccentrically mounted on said plate in such manner that a 90° phase difference exists between the compression strokes of said pistons.

5. An apparatus according to claim 4 wherein said rotatable plate is rotatable at different rates of speed to control the temperature in said first space.

6. An apparatus according to claim 2 wherein said means for reciprocating said pistons includes means rotatable in one direction for cooling said first space and rotatable in an opposite direction for heating said first space.

7. An apparatus according to claim 2 wherein said first conduit means is wrapped around a portion of said housing containing said second space thereby pre-cooling said refrigerant prior to its entry into said intermediate space.

8. An apparatus according to claim 2 wherein said regenerator is a multi-stage regenerator with the portion of said multi-stage regenerator in direct communication with said intermediate space forming the first stage and having the largest size, subsequent stages being axially aligned with the first stage and being progressively smaller.

9. A device for use in a cryosurgical operation comprising:
a housing having an interior wall defining a bore with first, intermediate, and second spaces defined therein;
first means connected to a portion of said housing containing said intermediate space for establishing communication between said intermediate space and first means for compressing a refrigerant;
second means connected to a portion of said housing containing said second space for establishing communication between said second space and second means for compressing a refrigerant, said first and said second means being adapted to interconnect said housing and said first and said second means for compressing a refrigerant to form a closed system using a Stirling cycle to selectively cool and heat refrigerant;
a displacer positioned in said bore for reciprocal movement and having a regenerator in communication with said intermediate and said first spaces;
first and second seal means for supporting said displacer in a position radially spaced from the wall of said housing, said first seal means separating said first and said intermediate spaces, and said second seal means separating said intermediate and said second spaces;
a cryosurgical operating tool positioned on a portion of said housing containing said first space, said tool being in heat exchange relationship with said first space so that said tool is selectively heated and cooled by refrigerant in said first space, said first space being adapted to receive, through said intermediate space and said regenerator, refrigerant compressed by the first means for compressing a refrigerant, the compressed refrigerant expanding and cooling said first space thereby cooling said operating tool, said second space being adapted to receive refrigerant compressed by said second means for compressing a refrigerant in such manner that the refrigerant prevents contact between an end of said housing and said displacer.

10. A device as claimed in claim 9 wherein said regenerator is a multi-stage regenerator having a first stage in direct communication with said intermediate space and a second smaller stage connected to the first stage, said first and second stages being coaxial.

11. A method of controlling the temperature of an operating instrument used in a cryosurgical operation, the method using a Stirling operating cycle and comprising:
(1) pre-charging an operating system with refrigerant to a pressure of approximately 150 psi, the operating system having:
(a) a compressor section having two cylinders spaced 90° from each other and containing pistons, one of said pistons being larger than the other, and means for reciprocating said pistons in said cylinders;
(b) an operating device having a displacer radially spaced from and mounted for reciprocal movement in a bore defined by a housing, a first seal positioned in the housing for supporting the displacer and for separating an intermediate space from a first space within the bore, a second seal positioned in the housing for supporting the displacer and for separating the intermediate space from a second space within the bore, and an operating instrument supported by the housing and in heat exchange relationship with the first space, the displacer including a regenerator having one passageway communicating with the intermediate space and one passageway communicating with the first space;

(c) a first flexible conduit interconnecting the cylinder containing the larger piston and the intermediate space so that refrigerant compressed by the larger piston expands and cools the first space thereby cooling the operating instrument; and (d) a second flexible conduit interconnecting the cylinder containing the smaller piston and the second space so that pressure within the second space prevents contact between the housing and the displacer;

(2) pre-cooling the operating instrument by reciprocating said pistons at a rate of between 1200 and 1500 reciprocations a minute and with a 90° phase difference thereby compressing the refrigerant in the cylinder containing the larger piston to a pressure of approximately 300 psi; and (3) varying the rate of reciprocation of said pistons to obtain a desired cryogenic temperature for the operating instrument.

12. A method according to claim 11 wherein the operating system includes a member rotatable about an axis and the pistons have arms connected to the rotatable member for eccentric rotation about the axis of the rotatable member, the pistons being reciprocated during a cooling operation by rotation of the rotatable member in a first direction, said method further comprising rotating the rotatable member in a direction opposite the first direction thereby heating the operating instrument and facilitating its removal at the completion of a cryosurgical operation.

13. An apparatus for use in a cryogenic surgical operation, the apparatus comprising a closed fluidically controlled Stirling cycle cooling system having a compression portion, a distinct expansion portion, and flexible conduit means for interconnecting the compression and expansion portions, said compression portion comprising:

a first piston positioned in a first cylinder,
a second piston smaller than said first piston positioned in a second cylinder, and
means for reciprocally moving said pistons to vary pressure in said cylinders;

said expansion portion comprising:
a third cylinder having distinct first, intermediate, and second spaces defined therein,
a third piston positioned in said third cylinder having opposite ends positioned in said first and second spaces, respectively, said third piston being displaceable in said third cylinder by pressure variations resulting from movement of said first and second pistons,
a regenerator positioned in said end of said third cylinder which is in said first space, the regenerator being in communication with said intermediate and said first spaces, and
an exterior portion of said third cylinder being in heat exchange relationship with said first space and defining a probe for use in a cryogenic surgical operation; and said flexible conduit means comprising:
first conduit means for interconnecting said first cylinder and said intermediate space, and
second conduit means for interconnecting said second cylinder and said second space, said means for reciprocally moving said pistons moving said first and said second pistons with a predetermined phase difference and cooperating with said flexible conduit means interconnecting said compression and expansion portions in such manner that the pressure in said second space initially assists and then opposes movement of said third piston from said first space towards said second space.

14. An apparatus as claimed in claim 13 wherein said means for reciprocally moving said pistons moves said pistons with a 90° phase difference therebetween.

* * * * *